United States Patent [19]

Thomas et al.

[11] 3,931,274
[45] Jan. 6, 1976

[54] BIS(2,3-DIBROMOPROPYL CARBONATES) OF TETRAHALOBISPHENOL A

[75] Inventors: Robert M. Thomas, Palisades Park, N.J.; Rastko I. Mamuzic, West Lafayette, Ind.

[73] Assignee: Great Lakes Chemical Corporation, West Lafayette, Ind.

[22] Filed: Mar. 27, 1973

[21] Appl. No.: 345,435

[52] U.S. Cl............ 260/463; 260/45.7 R; 260/42.37; 260/45.75 R; 260/45.85
[51] Int. Cl.$^2$ .................. C07C 69/96; C08K 5/10; C08K 5/159; C08K 3/36
[58] Field of Search ................................ 260/463

[56] References Cited
UNITED STATES PATENTS

| | | | |
|---|---|---|---|
| 3,218,347 | 11/1965 | Baker................................ | 260/463 |
| 3,267,070 | 8/1966 | Tousignant et al. ............. | 260/45.85 |
| 3,688,001 | 8/1972 | Exner et al. ...................... | 260/463 |
| 3,804,792 | 4/1974 | Pews................................. | 260/31.6 |

OTHER PUBLICATIONS
Chemical Abstracts, 7th Collective Index, p. 18,592s, 1-propanol, 2,3-dibromo (1970).

*Primary Examiner*—Donald G. Daus
*Assistant Examiner*—Diana G. Rivers
*Attorney, Agent, or Firm*—Laurence, Stokes & Neilan

[57] ABSTRACT

The compounds bis(2,3-dibromopropyl carbonate) of tetrabromobisphenol A and bis(2,3-dibromopropyl carbonate) of tetrachlorobisphenol A are effective fire retardants and impart enhanced fire-retardant properties to normally-combustible polymers by incorporation therein of a fire-retardant amount of one of said compounds or a mixture thereof. The fire retardancy of such polymer composition is further enhanced by incorporation therein of an additional flame-retardant material, e.g., an arsenic, antimony, or bismuth compound, preferably antimony oxide. Such polymer compositions of enhanced fire-retardancy incorporating a compound of the invention.

3 Claims, No Drawings

BIS(2,3-DIBROMOPROPYL CARBONATES) OF TETRAHALOBISPHENOL A

BACKGROUND OF INVENTION

1. Field of Invention

Certain bis(2,3-dibromopropyl carbonates) of tetrahalobisphenol A; their use as fire-retardants; polymeric compositions embodying the same.

2. Prior Art

This invention relates to novel compounds and to flame retardant polymer compositions containing the novel compounds.

Flame retardant polymeric materials are in great demand. To improve the flame retardant or flame-out property of a polymer so that it will not support combustion beyond a few seconds is an objective of the entire polymer and polymer-related industry.

In the art of thermoplastics, many materials have been suggested as additives for imparting fire-retardant properties. Many of these additives have been halogen-containing compounds and some have been successful in rendering thermoplastics fire-retardant. It would seem that to merely increase the amount of these known additives would be sufficient to achieve the desired flame-retardant property whereby flame-out would occur in a matter of only a few seconds. However, achievement of the desired flame-retardant property by using large quantities of known flame retardants results in diminution of the other desirable properties of the polymer. In many instances, increasing the amounts of known flame-retardant compounds does not improve the flame-out property of the polymer. Moreover, merely increasing the amount of halogen in a material does not result in improved fire- or flame-retardant properties. This merely increases cost, without any guarantee of improved fire-retardant effect. It is apparent that, for enhanced fire-retardant properties, specifically-tailored molecules are required, rather than merely more of the same retardant or additional halogen in an existing retardant, but just how such molecules should be tailored is not clear. Nevertheless it is clear that new fire-retardant materials are required and it would be most desirable to have not only an improved fire-retardant additive and polymer composition, but to have such an economic additive and composition whereby and wherein other desirable properties of the polymer are not seriously diminished by addition of the flame-retardant agent.

SUMMARY OF THE INVENTION

This invention relates to novel fire-retardant compounds and to novel polymeric compositions having enhanced fire-resistant properties incorporating one or more of said compounds. In one embodiment, this invention relates to fire-retardant compositions comprising a normally combustible polymer and a fire-retardant amount of bis(2,3-dibromopropyl carbonate) of tetrabromobisphenol A, or bis(2,3-dibromopropyl carbonate) of tetrachlorobisphenol A, or a mixture thereof. In a preferred embodiment, the degree of fire-retardancy is improved by additionally employing an arsenic, antimony, or bismuth compound, preferably antimony oxide.

OBJECTS

It is an object of this invention to provide novel compounds.

Another object of this invention is to provide improved fire-retardant polymer compositions.

Still another object of this invention is to provide such fire-retardant polymer compositions comprising one or more of the novel compounds of the invention.

Other objects and advantages of this invention will be obvious to one skilled in the art and still others will become apparent from the following detailed description.

DESCRIPTION OF INVENTION

Briefly, according to this invention, the foregoing and other objects are attained by provision of the stated novel compounds of the invention and by uniformly blending one or more thereof with a selected polymer to provide improved flame-retardant polymer compositions.

The novel compounds of the invention have already been set forth, as well as the fact of their flame-retardant properties. Further, in accord with this invention, normally combustible polymers are rendered more fire-retardant by incorporating therein a fire-retardant amount of one or more of the same. Thus, the compounds of this invention are generally useful on appropriate formulation by one skilled in the art to confer enhanced flame retardancy to polymeric materials and are desirably incorporated into such polymer materials in the range from about 2 to about 30 percent by weight of the polymer composition, and preferably about 6 to about 20 percent by weight. An antimony compound such as antimony oxide can be used, preferably in amounts in the range from about 1 to about 15 percent by weight of the polymer composition, and preferably about 3 to about 10 percent by weight of the polymer composition to enhance the flame retardant efficiency of the compounds of the present invention and polymeric compositions containing the same. Most broadly speaking, the compounds of the invention are incorporated into polymeric materials in an amount which can vary from about 1 to about 50 percent by weight of the polymer composition, preferably about 2 to about 30 percent by weight, and more preferably about 6 to about 20 percent by weight, i.e., in an effective fire-retardant proportion.

The components comprising the compositions of the present invention can be mixed by any one of several methods. A compound of the invention or mixtures thereof, if desired together with other additives, can be introduced into the polymer while the latter is dissolved in a suitable solvent. This procedure is especially useful when it is desired to mix the additives during the polymer manufacturing process. When the polymer is subsequently recovered from the solvent, the additives are intimately mixed with the polymer. Usually, the additives are mixed with the polymer in the molten state at temperatures that can range from the melting point to the decomposition temperature of the polymer. Alternatively, the additives and polymer are dry blended in the finely divided state so that an intimate mixture is obtained upon subsequent molding or extrusion.

Other metallic compounds are also suitable for use in improving the flame-retardant effectiveness of the compounds of the invention, such as those described in U.S. Pat. No. 3,634,311, including ammonium hexafluorotitanate, ammonium hexafluoroferrate, and mixtures thereof. It is also contemplated that other conventional flame retardants including, but not limited to, phosphate esters, alkyl diaryl phosphates, cresol diphenyl phosphate, octayl diphenyl phosphate, triaryl phosphates, tributyl phosphate, triphenyl phosphate, phosphonate esters, barium metaborate, zinc borate, boric acid, dibutyl tin maleate, etc., may be used in conjunction with the flame-retardant compounds of the present invention.

Still other additives usual to organic polymer compositions such as heat stabilizers, light stabilizers, fillers, plasticizers, pigments, etc., may also be present. For example, silica filler or the like may be added in small amounts, for example about 1 to 10 percent of the total polymer composition, to improve the drip characteristics of flammable polymers, such as polypropylene and polyethylene.

Typical normally-combustible polymers in which the compounds of this invention may be employed as an additive are homopolymers and copolymers of ethylenically unsaturated aliphatic, alicyclic and aromatic hydrocarbons such as polyethylene, polypropylene, polybutene, ethylene-propylene copolymers; copolymers of ethylene or propylene with other olefins, polybutadiene; polymers of butadiene, polyisoprene, both natural and synthetic, polystyrene and polymers of pentene, hexene, heptene, octene, 2-methylpropene; 1,4-methylhexene-1, bicyclo-(2.2.1)-2-heptene, pentadiene, hexadiene, 2,3-dimethylbutadiene-1,3; 4-vinylcyclohexene, cyclopentadiene, methylstyrene, and the like. Other polymers include polyindene, indenecoumarone resins; polymers of acrylate esters and polymers of methacrylate esters, acrylate and methacrylate resins such as from ethyl acrylate, n-butyl methacrylate, isobutyl methacrylate, ethyl metharcylate and methyl methacrylate, alkyd resins; cellulose derivatives such as cellulose acetate, cellulose acetate butyrate, cellulose nitrate, ethyl cellulose, hydroxyethyl cellulose, methyl cellulose and sodium carboxymethyl cellulose, epoxy resins; furan resins (furfuryl alcohol or furfural-ketone); hydrocarbon resins from petroleum, isobutylene resins (polyisobutylene); isocyanate resins (polyurethanes); melamine resins such as melamine-formaldehyde and malamine-urea-formaldehyde; oleoresins; phenolic resins such as phenol-formaldehyde, phenolic-elastomer, phenolic-epoxy, phenolic-polyamide, and phenolic-vinyl acetals; polyamide resins such as polyamides and polyamide-epoxy; polyester resins such as polyesters (unsaturated) of dibasic acids and dihydroxy compounds, and polyester elastomer and resorcinol resins such as resorcinol-formaldehyde, resorcinol furfural, resorcinol-phenol-formaldehyde, resorcinol-polyamide and resorcinol-urea; rubbers such as natural rubber, synthetic polyisoprene, reclaimed rubber, polybutadiene, cyclized rubber, butadiene-acrylonitrile rubber, butadiene-styrene rubber, and butyl rubber; polysulfides (Thiokol); terpene resins; urea resins; vinyl resins such as polymers of vinyl acetal, vinyl acetate or vinyl alcohol-acetate vinyl acetate copolymer, vinyl alcohol, vinyl butyral, vinyl chloride-acetate copolymer and vinyl pyrrolidone; polyformaldehyde; nylon, polycarbonates of dihydroxy compounds such as formed from bisphenols and phosgene, and thermoplastic polymers of bisphenols and epichlorohydrin (trade named Phenoxy polymers); bitumens and asphalts; and graft copolymers of polymers of unsaturated hydrocarbons and an unsaturated monomer.

Thus, the novel compounds of the invention will, as hereinbefore set forth, be useful as additives to plastics, polymers, co-polymers, terpolymers, resins, elastomers, rubbers, textiles and fibers, both naturally occurring and synthetic in nature, such as cotton, wool, Dacron, nylon, rayon, etc., coatings, paints, varnishes, leather, foams, polyolefins such as polyethylene and polyethylene copolymers, polypropylene and polypropylene copolymers, polystyrene co-polymers, polyvinyl acetate or alcohol and co-polymers, polyesters, polyurethanes, polyphenyl ethers, polycarbonates, polyamides, polyoxymethylenes, polyalkylene oxides, such as polyethylene oxide, polyacrylate and polymethacrylate copolymers with styrene, butadiene, acrylonitrile, etc., acrylonitrile-butadiene-styrene formulations (commonly known as ABS), polybutylene and acrylic ester modified styrene-acrylonitrile (ASA), methylmethacrylate-styrene-butadiene terpolymers, etc., whereby desirable physical characteristics of enhanced flame-proofing or fire retardancy will be imparted to the aforementioned materials.

As already stated, the improved fire retardancy of the normally combustible polymers can be further improved, if desired, by incorporating metallic compounds such as compounds of arsenic, antimony or bismuth in addition to the compounds of the present invention in the polymers. Antimony oxide is generally the antimony compound of choice. However, many antimony compounds are suitable. Suitable antimony compounds include the sulfides of antimony, antimony salts of the alkali metals of Group I of the Periodic Table, antimony salts of organic acids and their pentavalent derivatives and the esters of antimonous acids and their pentavalent derivatives. It is sometimes convenient to use sodium antimonite or potassium antimonite when it is desired to use an alkali metal salt of the antimonly. U.S. Pat. No. 2,996,528 discloses suitable antimony salts of organic acids and their pentavalent derivatives. Compounds of this class include antimony butyrate, antimony valerate, antimony caproate, antimony heptylate, antimony caprylate, antimony pelargonate, antimony caprate, antimony cinnamate, antimony anisate, and their pentavalent dihalide derivatives. Likewise, the esters of antimonous acids and their pentavalent derivatives disclosed in U.S. Pat. No. 2,993,924, such as tris(n-octyl) antimonite, tris(2-ethylhexyl) antimonite, tribenzyl antimonite, tris(beta-chloroethyl)antimonite tris(beta-chloropropyl) antimonite, tris(beta-chlorobutyl) antimonite, and their pentavalent dihalide derivatives. Still other suitable organic antimony compounds are the cyclic antimonites such as trimethylol propane antimonite, pentaerythritol antimonite and glycerol antimonite. The corresponding arsenic and bismuth compounds can also be employed, in particular the oxides of arsenic and bismuth. The metallic additives are generally employed in a proportion of about 1 to 15 percent by weight, preferably about 3 to 10 percent by weight of the polymer composition.

The compositions of the invention are also useful in protective coatings such as paints, varnishes, applications for insulated wire and cable fabric coatings, roofing materials and the like. Aside from imparting enhanced fire retardancy to normally combustible polymers, the additives also function as a reinforcing filler for improving such properites as flexural strength and modulus and heat deflection temperatures. The fire retardant compositions of the instant invention may be used in the preparation of plastic articles in general and reinforced plastic articles containing a reinforcement such as cloth, glass fibers in the form of roving, individual glass fibers, etc. Suitable reinforcements for preparing reinforced articles include textile fibers, glass fibers or cloth, roving, wood flour, mineral fillers, etc. In general, well-known processes of the prior art can be used for preparing the above-mentioned plastic articles and reinforced plastic articles, with the exception of substituting the compositions of the invention for that conventionally used. Usually, other changes in the process are not necessary.

The following are additional examples of suitable reinforcing media and fillers which can be used with the compositions of the invention: glass fibers, glass mats, glass cloth, synthetic fibers such as orlon, mineral fibers such as asbestos, natural fibers such as cotton, silk and wool, metallic fibers such as aluminum and steel, inorganic materials such as calcium carbonate, clay and pigments, and organic materials such as wood flour, cotton and ray flock, sisal fibers, and dyes.

DETAILED DESCRIPTION OF THE INVENTION

The following Preparations and Examples are given by way of illustration only and are not to be construed as limiting.

EXAMPLE 1

Bis(2,3-dibromopropyl caronate) of Tetrabromobisphenol A

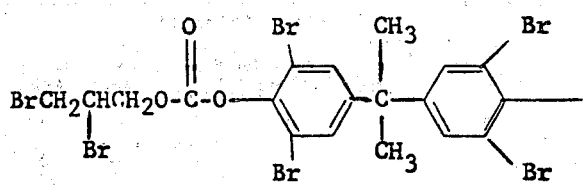
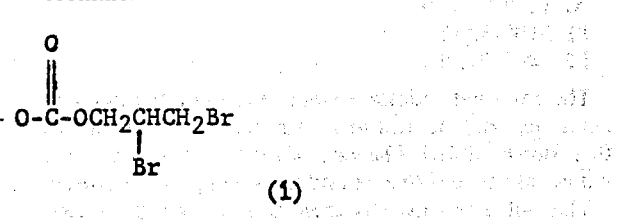
(1)

Preparation 1

The starting material, 2,3-dibromopropyl chloroformate, is prepared according to the method of R. Levaillant (*Ann.Chim* [11] 6, 505 (1936); Beilstein 3, III 26. This method comprises the reaction of 2,3-dibromopropanol and phosgene at temperatures in the range of 5°–40°C.

After several hours of reaction, unreacted phosgene and entrained hydrogen chloride are removed by vacuum stripping of the reaction mixture at 60°C. (17 mm Hg). Technical grade light yellow 2,3-dibromopropyl chloroformate is obtained, which is generally pure enough for direct use in the reactions described below. If a higher assay product is desired, technical-grade material may be distilled to afford 2,3-dibromopropyl chloroformate as a colorless, clear liquid, boiling point 90°–95°C./2 mm Hg (literature boiling point 127°–129°C./21 mm Hg).

Compound 1

To a mechanically stirred solution of 272 grams (0.50 mole) of 4,4'-isopropylidene bis(2,6-dibromophenol), i.e., tetrabromobisphenol A, in 1.4 liters of acetone at room temperature, was added 67.8 grams (1.05 mole) of potassium hydroxide (87% assay; slightly exothermic reaction). After the addition was complete, the mixture was stirred for ca. 1.5 hours at 30°C., and then heated to reflux and agitated for an additional 2 hours. At this point, a total of 315.2 grams of 2,3-dibromopropyl chloroformate (93.4% VPC assay), prepared as described in the foregoing, was added over a 20-minute period at a reaction temperature of 23°–49°C. The reaction mixture was then heated to reflux and maintained at that temperature for 2 hours, after which time the reaction mixture was cooled to room temperature. After standing overnight, the reaction mixture was stripped to dryness at 60°C. (17 mm Hg). A mixture of dichloromethane (2100 milliliters) and water (300 milliliters) was added to the remaining solids. After discarding the aqueous layer, the organic fraction was washed with four 100-milliliter portions of 5% (w/w) aqueous sodium hydroxide solution, and then with 100 milliliters of water. The washed organic layer was then stripped to dryness on a rotary evaporator at 60°C./17 mm Hg to give 524.3 grams of off-white bis(2,3-dibromopropyl carbonate) of tetrabromobisphenol A, melting point 159°C. Recrystallization from benzene, followed by methanol washing of the recrystallized product before drying, increased the melting point of the final product to 163.3°C. Two repetitions of this purification procedure improved the melting point to 164.1°C. Bromine elemental analysis of the triple-recrystallized material gave the following: Calculated for $C_{23}H_{20}Br_8O_6$: 62.0% bromine; Found: 60.5% bromine.

Infrared spectrum (potassium bromide pellet) displayed characteristic carbonyl absorption at 5.69 microns.

EXAMPLE 2

Bis(2,3-dibromopropyl carbonate) of Tetrachlorobisphenol A

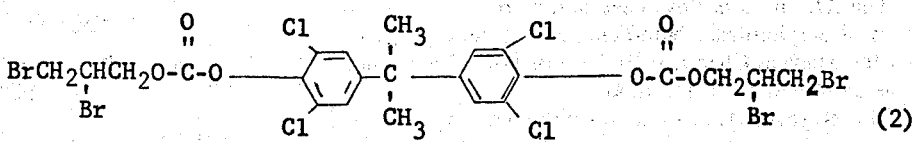
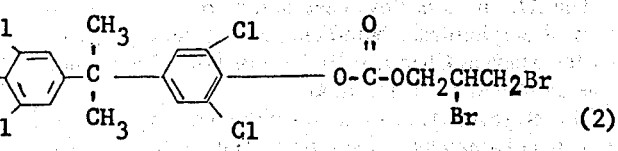
(2)

Compound 2

To a stirred solution of 366.1 grams (1.0 mole) of 4,4'-isopropylidenebis(2,6-dichlorophenol), i.e., tetrachlorobisphenol A, in 1.8 liters of acetone at room temperature, was rapidly added 135.4 grams (2.1 moles) of potassium hydroxide pellets (87% assay). After the addition was complete, the reaction mixture was stirred for ca. 30 minutes during which time the temperature rose to 38°C. The reaction mixture was then heated to reflux and maintained at that temperature for 2 hours. After this time, the reaction mixture was cooled to ca. 35°C. and a total of 625.8 grams of 2,3-dibromopropyl chloroformate (94.1% VPC assay) was then added over a 25-minute period at 35°–50°C. The reaction mixture was heated to reflux and maintained at that temperature for 2 hours, after which time the reaction mixture was stripped to dryness on a rotary evaporator at 60°C./17 mm Hg. The resulting pale ocher solid was then slurried in water, filtered, and the filter cake washed with water until the filtrate was essentially chloride free. Air-drying of the filter cake to constant weight afforded 836.8 grams of light yellow bis(2,3-dibromopropyl carbonate) of tetrachlorobisphenol A, melting point 136°C. The technical grade product was then slurried in excess methanol at room temperature to give white crystalline product with a melting point of 145.0°C. Elemental analysis of this material gave the following: Calculated for $C_{23}H_{20}Br_4Cl_4O_6$: 37.4% bromine, 16.6% chlorine; Found: 35.7% bromine, 16.9% chlorine.

The infrared spectrum (potassium bromide pellet) exhibited characteristic carbonyl absorption at 5.65 microns.

Flame-Retardant Evaluation Data

To illustrate the flame-retardant effectiveness of these compounds, the foregoing carbonates were incorporated into several polymers in the following manner:

One hundred parts of polypropylene (PP), high-impact styrene (IS), acrylonitrile-butadiene-styrene polymer (ABS) or polyethylene (PE) were first banded on a two-roll mill (rear roll: front roll friction ratio = 1.4:1.0; front roll speed — 23 rpm) at the approximate temperatures designated:

IS 260°–265°F
ABS 270°–275°F
PP 310°–320°F
PE 240°–245°F

The carbonate additive alone or in combination with antimony trioxide and/or commercial-grade silica was then slowly added. The rate of feed depends upon the nature of the additive or additives being incorporated.

The polymer mix was then molded in a preheated mold at the appropriate temperature for two minutes, pressed for three minutes, and then cooled for two minutes under pressure. Approximate press temperatures were as follows:

ABS, IS 325°F
PP 350°F
PE 275°F

The ABS used in this evaluation work was a copolymer of acrylonitrile, butadiene, and styrene prepared by the Marbon Chemical Division of Borg-Warner and was identified as "CYCOLAC T".

The polypropylene used was obtained from Rexene Polymers Company, a Division of Dart Industries, was identified as "EL REXENE PP 11S SERIES", and is reported to have a melt flow at 230°C. of 10g/10min (ASTM D 1238). A second sample of polypropylene "EL REXENE PP 11S SERIES" used in this work is reported to have a melt flow at 230°C. of 12g/10min.

The impact styrene used in this work was high-impact grade polymer prepared by Union Carbide Corporation and was identifed as "Union Carbide TMDE-6500."

The polyethylene used was low-density polymer prepared by Rexene Polymers Company, a Division of Dart Industries, and was identified as "PRODUCT 179" which is reported to have a nominal melt index of 12 and a nominal density of 0.917.

The flammability of the polymer specimens was then evaluated by A.S.T.M. D2863-70, "Flammability of Plastics using the Oxygen Index Method."

This widely-used flammability test determines the lowest concentration of oxygen (expressed as the Oxygen-Index) in a mixture of nitrogen and oxygen which is needed to sustain top burning of a vertical specimen. Oxygen-index values for a number of ABS, polypropylene, polyethylene, and impact styrene formulations are tabulated below.

Those additives which give rise to the highest oxygen-index values in polymer systems at the lowest loading levels are considered the most desirable.

I. FR Evaluation Data in ABS

FLAMMABILITY TEST DATA

| Flame Retardant Additive | Polymer | Parts/100 Parts Polymer Additive | $Sb_2O_3$ | Silica | Oxygen Index |
|---|---|---|---|---|---|
| None | ABS | — | — | — | 18.5 |
| Compound 1 | " | 12 | — | — | 21.0 |
| " | " | 12 | 3 | — | 24.1 |
| " | " | 12 | 5 | — | 24.5 |
| " | " | 16 | 5 | — | 25.7 |
| Compound 2 | " | 12 | — | — | 21.8 |
| " | " | 12 | 3 | — | 23.3 |
| Octabromo-Biphenyl | " | 12 | — | — | 20.7 |
| " | " | 12 | 3 | — | 22.5 |
| Bis(Tribromo-Phenyl) Carbonate | " | 12 | — | — | 20.4 |
| " | " | 12 | 3 | — | 21.9 |

II FR Evaluation Data in Polypropylene

FLAMMABILITY TEST DATA

| Flame Retardant Additive | Polymer | Parts/100 Parts Polymer Additive | $Sb_2O_3$ | Silica* | Oxygen Index |
|---|---|---|---|---|---|
| None | PP | — | — | — | 18.0 |
| Compound 1 | " | 12 | — | — | — |
| " | " | 12 | 3 | — | 25.1 |
| " | " | 12 | 3 | 1 | 27.2 |
| " | " | 12 | 3 | 3 | 25.8 |
| " | " | 12 | 3 | 5 | 25.3 |
| Compound 2 | " | 12 | — | — | — |
| " | " | 12 | 3 | — | 25.6 |
| " | " | 12 | 3 | 3 | 24.5 |
| Hexabromo-Benzene | " | 12 | — | — | 22.5 |
| " | " | 12 | 3 | — | 22.9 |
| Octabromo-Biphenyl | PP | 12 | — | — | 22.7 |
| " | " | 12 | 3 | — | 22.1 |

I. FR Evaluation Data in ABS

FLAMMABILITY TEST DATA

| Flame Retardant Additive | Polymer | Parts/100 Parts Polymer Additive | $Sb_2O_3$ | Silica | Oxygen Index |
|---|---|---|---|---|---|
| None | ABS | — | — | — | 18.5 |
| Compound 1 | " | 12 | — | — | 21.0 |
| " | " | 12 | 3 | — | 24.1 |
| " | " | 12 | 5 | — | 24.5 |
| " | " | 16 | 5 | — | 25.7 |
| Compound 2 | " | 12 | — | — | 21.8 |
| " | " | 12 | 3 | — | 23.3 |
| Octabromo-Biphenyl | " | 12 | — | — | 20.7 |
| " | " | 12 | 3 | — | 22.5 |
| Bis(Tribromo-Phenyl) Carbonate | " | 12 | — | — | 20.4 |
| " | " | 12 | 3 | — | 21.9 |

II FR Evaluation Data in Polypropylene

FLAMMABILITY TEST DATA

| Flame Retardant Additive | Polymer | Parts/100 Parts Polymer Additive | $Sb_2O_3$ | Silica* | Oxygen Index |
|---|---|---|---|---|---|
| None | PP | — | — | — | 18.0 |
| Compound 1 | " | 12 | — | — | — |
| " | " | 12 | 3 | — | 25.1 |
| " | " | 12 | 3 | 1 | 27.2 |

I. FR Evaluation Data in ABS-continued

FLAMMABILITY TEST DATA

| Flame Retardant Additive | Polymer | Parts/100 Parts Polymer Additive | $Sb_2O_3$ | Silica | Oxygen Index |
|---|---|---|---|---|---|
| " | " | 12 | 3 | 3 | 25.8 |
| " | " | 12 | 3 | 5 | 25.3 |
| Compound 2 | " | 12 | — | — | — |
| " | " | 12 | 3 | — | 25.6 |
| " | " | 12 | 3 | 3 | 24.5 |
| Hexabromo-Benzene | " | 12 | — | — | 22.5 |
| " | " | 12 | 3 | — | 22.9 |
| Octabromo-Biphenyl | PP | 12 | — | — | 22.7 |
| " | " | 12 | 3 | — | 22.1 |

*Silica was obtained from PPG Industries and was identified as HI-SIL 233.

In addition, at loading levels of 6 phr of flame retardant and 3 phr of antimony oxide, both Compounds 1 and 2 compared favorably with a commercial flame-retarded PP and appeared somewhat advantageous compared with a related but more expensive flame-retardant material.

III FR Evaluation Data in Polyethylene

FLAMMABILITY TEST DATA

| Flame Retardant Additive | Polymer | Additive | $Sb_2O_3$ | Silica | Oxygen Index |
|---|---|---|---|---|---|
| None | PE | — | — | — | 18.9 |
| Compound 1 | " | 6 | 3 | — | 26.0 |
| " | " | 12 | 3 | — | 25.0 |
| " | " | 12 | 6 | — | 27.1 |
| Compound 2 | " | 6 | 3 | — | 24.3 |
| " | " | 12 | 3 | — | 24.0 |
| " | " | 12 | 6 | — | 25.4 |

In addition, at loading levels of 6 phr of flame retardant and 3 phr of antimony oxide, both Compounds 1 and 2 compared favorably with a commercial flame-retarded PE and were approximately equivalent to a related but more expensive flame-retardant material.

IV FR Evaluation Data in Impact Styrene

FLAMMABILITY TEST DATA

| Flame Retardant Additive | Polymer | Additive | $Sb_2O_3$ | Silica | oxygen Index |
|---|---|---|---|---|---|
| None | IS | — | — | — | 18.1 |
| Compound 1 | " | 12 | — | — | 20.5 |
| " | " | 12 | 3 | — | 21.8 |
| Compound 2 | " | 12 | — | — | 20.0 |
| " | " | 12 | 3 | — | 21.1 |

The present invention is not to be limited to the exact details of operation or exact compounds, compositions, methods, or procedures shown and described, since only preferred forms have been described herein and various modifications and substitutions of equivalents will be apparent to one skilled in the art and can be made without departing from the spirit or scope thereof.

We claim:

1. A compound selected from the group consisting of (a) bis(2,3-dibromopropyl carbonate) of tetrabromobisphenol A and (b) bis(2,3-dibromopropyl carbonate) of tetrachlorobisphenol A.

2. A compound of claim 1 which is bis(2,3-dibromopropyl carbonate) of tetrabromobisphenol A.

3. A compound of claim 1 which is bis(2,3-dibromopropyl carbonate) of tetrachlorobisphenol A.

* * * * *